United States Patent [19]
Casper et al.

[11] Patent Number: 5,826,571
[45] Date of Patent: Oct. 27, 1998

[54] DEVICE FOR USE WITH METERED DOSE INHALERS (MDIS)

[75] Inventors: Robert A. Casper, Raleigh; Frank A. Leith; David L. Gardner, both of Chapel Hill, all of N.C.

[73] Assignee: Innovative Devices, LLC, Raleigh, N.C.

[21] Appl. No.: 659,723

[22] Filed: Jun. 6, 1996

Related U.S. Application Data

[60] Provisional application No. 60/000,086 Jun. 8, 1995.

[51] Int. Cl.⁶ .................................................. A61M 11/00
[52] U.S. Cl. ................................ 128/200.23; 128/200.14
[58] Field of Search ........................ 128/200.14, 200.18, 128/200.23, 203.12, 203.15

[56] References Cited

U.S. PATENT DOCUMENTS

| | | | |
|---|---|---|---|
| 3,900,138 | 8/1975 | Phillips | 128/200.14 |
| 4,817,822 | 4/1989 | Rand et al. | 128/200.14 |
| 5,033,463 | 7/1991 | Cocozza | 128/203.21 |
| 5,069,204 | 12/1991 | Smith et al. | 128/200.23 |
| 5,119,806 | 6/1992 | Palson et al. | 128/200.14 |
| 5,217,004 | 6/1993 | Blasnik et al. | 128/200.14 |
| 5,349,945 | 9/1994 | Wass et al. | 128/200.14 |
| 5,408,994 | 4/1995 | Wass et al. | 128/203.15 |
| 5,447,150 | 9/1995 | Bacon | 128/200.14 |
| 5,482,030 | 1/1996 | Klein | 128/200.23 |

FOREIGN PATENT DOCUMENTS

| | | | |
|---|---|---|---|
| 186280 | 2/1986 | European Pat. Off. | 128/200.14 |

*Primary Examiner*—John G. Weiss
*Assistant Examiner*—William J. Deane, Jr.
*Attorney, Agent, or Firm*—Thorpe, North & Western, L.L.P.

[57] ABSTRACT

An inhalation device is provided for use with pressurized metered dose inhalers (MDIs). The device includes a mechanical mechanism for applying the force required to discharge the MDI, a breath-activated trigger for activating this mechanical mechanism, an auto-return mechanism for insuring recovery of the aerosol canister from the fired position and a dose counter for counting the doses dispensed or available. Arming of the device is achieved by removing the protective mouthpiece cover/dust cap. Activation of the MDI is set to occur at a point subsequent to the beginning of inhalation.

18 Claims, 2 Drawing Sheets

DEVICE FOR USE WITH METERED DOSE INHALERS (MDIS)

RELATED APPLICATIONS

This is an application filed under 35 U.S.C. §111(a) for an invention which was disclosed in Provisional Application Serial No. 60/000,086, filed under 35 U.S.C. §111(b) on Jun. 8, 1995, no more than twelve (12) months from the filing dated of this §111(a) application.

TECHNICAL FIELD

The present invention relates to inhalation-or breath-activated devices for use with metered dose inhalers (MDIs) comprised of an aerosol canister which contains medicament for administration to the lungs and a dispenser (actuator) supplied with the aerosol canister, through which a series of metered medicament doses can be dispensed. In particular, the invention relates to inhalation or breath-activated devices for use with MDIs, which are mechanical in the nature of their operation and incorporate an auto-return mechanism to ensure recovery of the aerosol canister from the fired position without the need for intervention by the user. Further, the invention particularly relates to inhalation or breath-activated devices for use with metered dose inhalers which are readied for use by opening a protective mouthpiece cover/dust cap or similar mechanism.

RELATED ART

Inhalation or breath-activated devices for use with aerosol canisters are known, the purpose of which is to provide proper coordination of dispensing a dose of medicament with the inhalation of the user, thus providing for the maximum proportion of the dose of medicament to be deposited in the lungs.

Devices for the delivery of aerosol-based medications by the inhalation route are known. One such frequently used device is a metered dose inhaler, consisting of a pressurized aerosol canister (reservoir) of medication containing a fixed volume metering chamber (valve) which is inserted into a housing having a receptacle adapted to receive the stem of the valve of the aerosol canister. The housing has a nose-piece or mouthpiece for delivering medication to the patient. The patient self-administers the medication by manually pressing down the aerosol canister into the housing causing movement of the canister relative to its stem (which is fixed in the stem block of the housing), resulting in venting of the canister's metering chamber (valve) and releasing the contents of the metering chamber, through the stem, through the stem block and its exit jet and orifice, causing the medication to exit the inhaler as an aerosol mist. Simultaneously with this action, the patient inhales through the housing, entraining the aerosol mist in the inhaled stream of air. The patient then releases the depression force on the aerosol canister and the canister, under the action of its internal valve spring, moves upward with respect to the valve stem, returning to its resting position. During this action the metering chamber becomes fluidly connected with the liquid contents of the aerosol canister and fills with that liquid, becoming ready for the next administration of medication. See for example, U.S. Pat. Nos. 3,001,524 and 3,012,555.

A major problem with the use of metered dose inhalers is the improper coordination exhibited by many patients in depressing the aerosol canister at a point during inhalation to optimize deposition of the medication in the lungs. Many people, especially children and the elderly, find this coordination difficult, actuating the inhaler too early or too late during inspiration, or actuating the inhaler during expiration.

Another device is the breath-activated inhaler which serves to automatically activate the aerosol canister and release the contents of the canister's metering chamber in response to a patient's inspiration, their general purpose being to alleviate the coordination of aerosol canister actuation with the patient's inspiration and providing for a maximal amount of medication to be drawn into the patients lungs. Examples of such devices are described in U.S. Pat. Nos. 5,404,871; 5,347,998; 5,284,133; 5,217,004; 5,119,806; 5,060,643; 4,664,107; 4,648,393; 3,789,843; 3,732,864; 3,636,949; 3,598,294; 3,565,070; 3,456,646; 3,456,645; 3,456,644; and British Patent Specification Nos. 2,061,116; 1,392,192; 1,335,378; 1,269,554 and German Patent No. 3,040,641.

Existing breath-activated inhalers are designed to accommodate available aerosol canisters separate from the receiving bodies or housings for which they were originally designed, marketed, and approved by the Food and Drug Administration (FDA). Aerosol medications of the pressurized inhaler type are drug products approved and regulated by the FDA as the combination of the pressurized aerosol canister and the housing (actuator) used to atomize the canister metering valve contents. The housing (actuator) is regarded as an integral part of the aerosol drug delivery system, since the design of the housing greatly influences the nature of the aerosol spray generated for inhalation by the patient. The design of the actuator impacts not only the amount of medication released from the inhaler, but the amount of medication received by the patient due to the actuator's influence on the particle size and velocity distribution of the emitted aerosol mist and the influence of the particle or droplet size distribution and velocity on impaction in the patient's respiratory tract. As a consequence, existing breath-activated inhalers must be approved by the FDA in conjunction with a particular aerosol-based medication canister. As a result, these inhalers have not been generally available to the patient public for use with the full range of aerosol-based medications which are available for the treatment and management of disease.

A problem with the mechanical breath-activated inhalers is that the aerosol canister remains in the depressed position, after firing by the inhaler's internal actuation mechanism, until the patient physically intervenes and relieves the mechanical load on the aerosol canister by moving a lever, strap, or some other mechanical means. Immediately after venting, the metering chamber (valve) of the aerosol canister becomes vulnerable to the intrusion of air and the extent of air intrusion increases with the length of time the canister remains in the depressed position. The intrusion of air in this fashion can result in "vapor locking" of the metering valve, resulting in incomplete filling of the metering chamber of the valve when the canister is ultimately released from the depressed position. Incomplete filling of the metering chamber, in turn, results in incomplete dosing on the next actuation of the inhaler, due to the lower quantity of drug which has entered the metering chamber from the liquid contents of the canister.

Another problem associated with some mechanical breath-activated inhalers is that the aerosol canister actuation mechanism must be in the "armed", ready to fire, position in order to allow recovery of the aerosol canister from the depressed position under the action of it's own internal valve spring. Two potential consequences may result from this condition. First, the actuation mechanism may be "armed" during the intervals between inhaler use or, of potentially more seriousness, the actuator mechanism may be "armed" during storage of the device (up to 3 years) if the device, as a consequence of its sale in combination with an aerosol canister as mandated by the FDA, is packaged with an aerosol canister in place. In either event, the functional life and reliability of the device may be compromised by the long term stress effects of maintaining the actuation mechanism in the "armed" position for extended periods. Second, the actuator mechanism may "relax" or creep, in either a fluid or bulk mechanical sense, if the device is stored for prolonged periods in the "armed" position, resulting in a change in actuator functionality with effects that may range from "premature" firing of the aerosol canister to delayed or extended firing time during the canister depression phase. In both cases the patient does not receive the prescribed dose of medication which the inhaler was designed to deliver.

Electro-mechanical inhalers are also known. U.S. Pat. No. 5,347,998 describes a breath-activated inhaler with an electro-mechanical priming mechanism. It is the object of the invention described therein to provide an inhalation device for use with pressurized aerosol canisters which does not require manual priming for firing the valve contained within the aerosol canister. Further, the inhaler provides an electro-mechanical means for relieving the firing load imposed on the aerosol canister during actuation.

U.S. Pat. No. 5,284,133 describes a dose timer, actuator mechanism, and patient compliance monitoring means. The invention relates to a dose or timing controlled actuator that operates in conjunction with an inhalation device to prevent both patient under-compliance with prescribed medication dosing and patient abuse of or dependence on prescribed medication. The invention contemplates the use of an actuator to prevent patient actuation of the inhalation device at non-prescribed intervals or at higher than prescribed doses, and the use of an alarm to notify the patient regarding undercompliance/underdosing situations and attempted abuse situations.

U.S. Pat. No. 5,404,871 describes an apparatus and method for delivering an amount of aerosolized medicine for inspiration by a patient in response to the occurrence of an appropriate delivery point or points in the patient's detected breath flow. Changes in a patient's breath flow pattern during the course of an aerosolized medication inspiration therapy program may be detected and used to adjust the controlled amount of medication to be delivered in a given administration and/or to conform to the pattern of the patient's condition or change in condition. The device may also contain a library of administration protocols or operating parameters for different medications and means for identifying, from the canister, the medicinal contents of the canister for customizing operation of the apparatus.

U.S. Pat. No. 5,497,764 describes a portable, battery powered, hand-held system for releasing a controlled dose of aerosol medication for inhalation by a patient including a durable body and an aerosol medication cassette inserted in the durable body. The durable body includes an actuator mechanism for engaging an inserted cassette and its canister, and an actuator release mechanism for controlling the actuator mechanism to depress the canister for a selected period of time to release the desired dose of medication and then release the canister. The actuator mechanism, includes a compression spring for depressing the canister and a torsion spring for reloading the compression spring. The torsion spring is reloaded by rotating the cassette from an open position for delivering aerosol to a closed position. The actuator release mechanism includes a motor and trigger pin assembly that controls the release of the compression spring and the torsion spring, and, hence, the time that the canister is depressed.

DISCLOSURE AND OBJECTS OF THE INVENTION

The present invention provides a device for use with a metered dose inhaler (comprising both the pressurized canister and actuator) for dispensing medicament from the metered dose inhaler. The device comprises a housing having a space therein for holding a metered dose inhaler with the space communicating with an opening for dispensing medicament therethrough from the metered dose inhaler. Means are provided for automatically activating a metered dose inhaler in response to inhalation of a user through the opening to vent the metered dose inhaler wherein a dose of medicament is dispensed therefrom. The device further includes return means for automatically deactivating a vented metered dose inhaler to its unvented position where medicament is no longer dispensed therefrom wherein the return means acts in response to the activating means. In the preferred embodiment, the housing comprises a hinged cap covering the opening when the cap is in a closed position and exposing the opening when the cap is in an open position. The cap is moveable from its closed position to its opened position to arm the means for depressing the metered dose inhaler. The device further includes control means for controlling the time of venting of a metered dose inhaler wherein the control means preferably comprises a deformable viscoelastic element.

It is therefore an object of the present invention to provide a novel inhalation device for use with metered dose inhalers (MDIs).

It is another object of the present invention to provide an inhalation device for use with MDIs which includes a mechanical mechanism for applying the force required to actuate a MDI at a preset patient inspiration flow rate, the MDI being physically incorporated into the present invention with the aerosol canister still housed in the actuator for which the medication has received FDA approval.

It is yet another object of the present invention to provide an auto-return mechanism for returning the aerosol canister of a MDI to the "resting" position within a brief time following actuation of the MDI in order to assure that the MDI is properly "primed" for administration of a subsequent dose.

It is a further object of the present invention to provide viscoelastic means for controlling the timing function of the auto-return mechanism.

It is yet a further object of the present invention to provide means for arming the mechanical MDI actuation mechanism, just prior to use, by incorporating the arming function with removal of a protective mouthpiece cover or dust cap.

It is a still further object of the present invention to provide a mechanical override mechanism by which the MDI may be actuated by the mechanical actuation mechanism without the necessity of the patient achieving the predetermined inspiration flow rate.

It is a still further object of the present invention to provide a dose-counting means associated with the MDI actuation to count the number of medicant doses dispensed or available from the aerosol canister.

Some of the objects of the invention having been stated hereinabove, other objects will become evident as the description proceeds, when taken in connection with the accompanying drawings as best described hereinbelow.

BEST MODE FOR CARRYING OUT THE INVENTION

Figure 1:
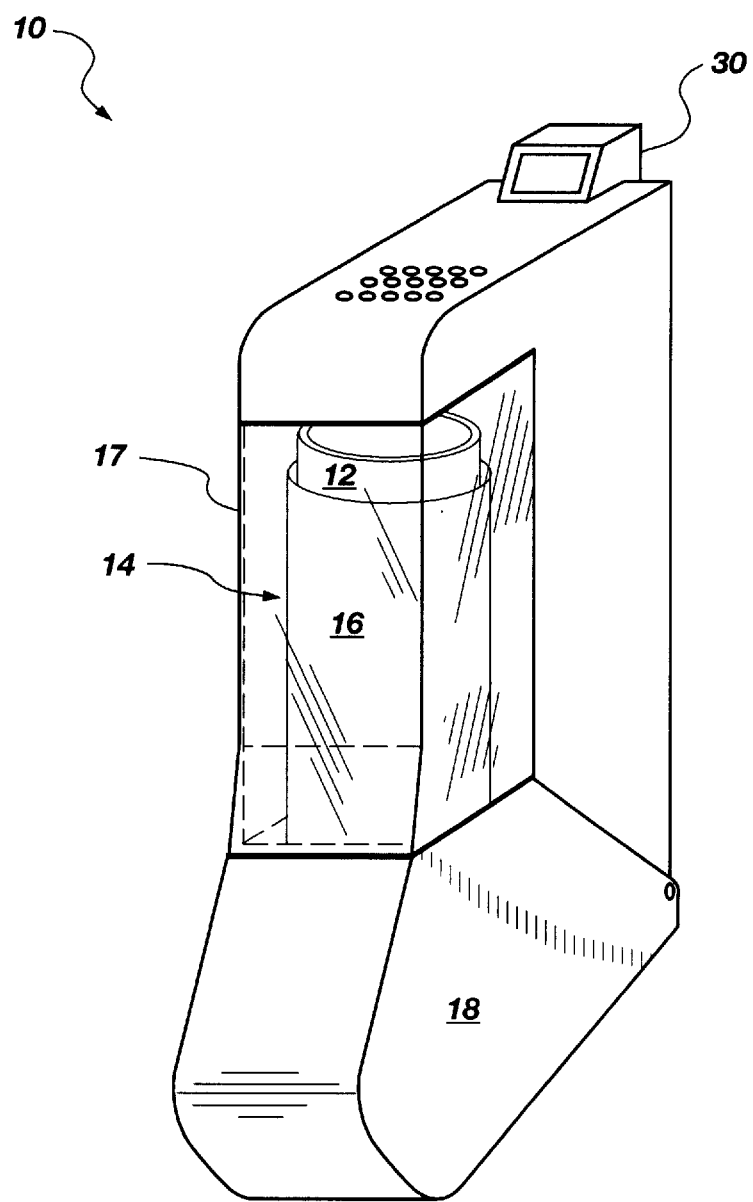
FIG. 1 of the drawings is a perspective view of the breath-activated inhalation device of the present invention.
Figure 2:
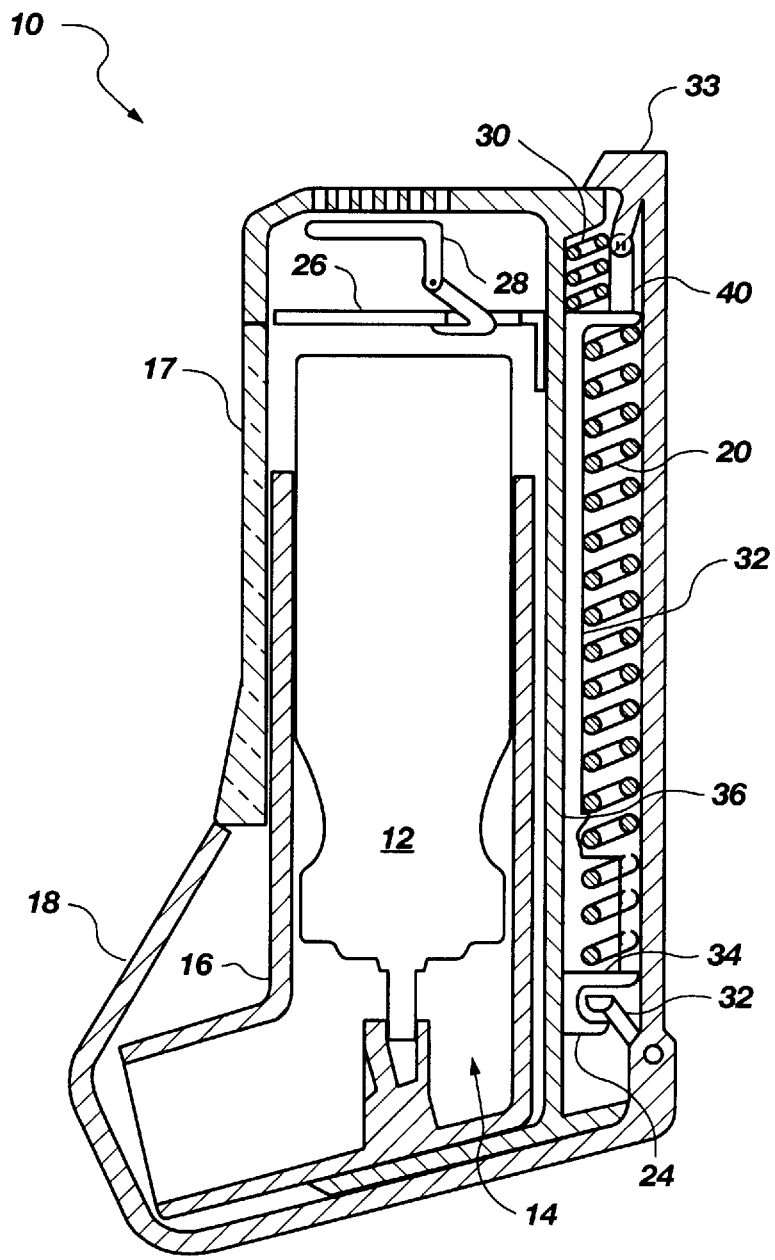
FIG. 2 of the drawings is a vertical cross section of the breath-activated inhalation device of FIG. 1.

Referring to FIGS. 1 and 2, the present invention provides a breath-activated inhalation device, generally designated 10, for mechanically actuating and restoring, to the "resting" position, an aerosol canister 12 of a metered dose inhaler (MDI), generally designated 14, under the action of a patient's inspiratory flow, thereby alleviating the difficulty most patients experience in coordinating inspiration with inhalation and manually actuating a MDI to achieve optimal deposition of medication in the lungs. MDI 14, consisting of medicament-containing aerosol canister 12 and its associated actuator 16, is incorporated directly into inhalation device 10 by the patient and may be used with a variety of different MDI products. The relationship between the MDI and breath-activated inhalation device 10 can be seen in FIGS. 1 and 2. Inhalation device 10 can include access panel 17 which can be used to insert and remove MDI 14 from inhalation device 10. Access panel 17 can be transparent in order to be able to see MDI 14 therethrough, but it is envisioned according to this invention that access panel 17 could be opaque as well.

"Arming" of the mechanical actuating mechanism of this invention may be initiated by a user by opening a mouthpiece cover or protective dust cap 18 which is operatively connected to power spring 20 by a latching mechanism. As shown in FIG. 2, the latching mechanism can comprise arm 22 and receiving member 24 for operatively receiving arm 22 and which is connected to power spring 20. Opening dust cap 18 latches and stretches power spring 20, the distal end of which is connected to an actuating platform 26 which is latched in the fixed position by a breath or inspiration-activated catch/release mechanism 28. Activating platform 26 is further connected to a weaker return spring 30, the distal end of which is affixed to the housing of device 10. When a user inhales and reaches a preset inspiration flow rate, breath-activated catch/release mechanism 28 releases actuating platform 26 and the force stored in "stretched" power spring 20 pulls actuating platform 26 downward, depressing and venting aerosol canister 12 housed in device 10 and releasing medicant contained therein as an aerosol mist.

Immediately or shortly after MDI 14 is actuated, receiving member 24 of the latching mechanism is released from its latched position with arm 22 by the action (contact) of rod 32 in attachment to actuating platform 26, and actuating platform 26, with power spring 20 and lower platform 34, moves upward under the retractive action of return spring 30. As actuating platform 26 proximally approaches its "resting" position it engages breath-activated catch/release mechanism 28 and becomes immobilized under the action of the latching means associated therewith. The upward movement of actuating platform 26 under the action of return spring 30 allows aerosol canister 12 to move upward under the action of its internal metering valve spring (not shown) to its "resting" position. During the course of the canister's movement upward, the metering chamber of aerosol canister 12 refills with fluid contents from the canister volume.

This auto-return feature of the present invention is an advance over other mechanical inhalers for which a user must intervene to return the aerosol canister to its resting position, either by "rearming" the device or by some other mechanism. In this case, there is no control over the period of time during which the aerosol canister remains in the depressed (vented) position. In the vented position a canister metering valve is subject to intrusion of air from the environment. If a canister remains in the vented position for too long, "vapor" locking of the metering valve may occur when the canister is finally released from the depressed position. In the prior art devices, all or a portion of the air in the metering chamber is not eliminated during the filling cycle and this remaining air displaces volume that would normally be filled with fluid from the canister contents. Consequently, a lower than specified dose of medicant is present in the metering chamber at the end of the filling cycle, manifested as a lower dosing of medication when the user next actuates the MDI.

Timing control of the venting period of the aerosol canister, such as aerosol canister 12, is achieved by incorporation of a viscoelastic element which serves to slow the downward movement of the actuating platform after venting of the aerosol canister has begun. In one embodiment and as shown in FIG. 2, the viscoelastic element is incorporated as a fixture, such as viscoelastic element 36, on lower platform 34 and is acted upon by rod 32 connected to actuating platform 26. The viscoelastic element may be polymeric in nature or may be constructed via a traditional spring and dashpot arrangement.

On actuation, power spring 20 provides the force for actuating the canister to ensure complete venting by movement of actuating platform 26 in a downward fashion. Rod 32 is integrated into actuating platform 26 and travels with actuating platform 26 as it moves downward. Within a short distance from its "resting", latched position, actuating platform 26 contacts aerosol canister 12 and pushes it downward under the influence of power spring 20. As canister 12 moves downward, its metering chamber moves axially with respect to the end of the valve stem until the metering chamber begins to vent its contents. Canister 12 continues its downward movement until rod 32, by means of an associated "stop", contacts viscoelastic element 36. The point of contact with viscoelastic element 36 preferably coincides with a point intermediate between the position at which the metering chamber vents and the point at which the aerosol canister valve spring (not shown) is fully compressed at its "bottom out" position. Upon contacting viscoelastic element 36, the downward motion of actuating platform 26 slows considerably, advancing downward under the influence of power spring 20 at a rate governed primarily by the time-dependent deformation of the viscoelastic material. This slowing of the downward motion of actuating platform 26 serves to provide the time required for complete venting of the metering chamber. Rod 32 continues to move slowly downward as viscoelastic element 36 deforms until rod 32 contacts lower platform 34 which can be a part of receiving member 24. At this point lower platform 34 is released from its latched and fixed position and actuating platform 26 is free to move upward under the influence of its return spring 30 and possibly even with assistance provided by the internal aerosol canister valve spring (not shown). As actuating platform 26 moves upward, lower platform 34 also moves upward under the action of the power spring 20. The aerosol canister metering chamber remains vented to the atmosphere until the upward movement of the canister results in sealing off of the stem connection between the metering chamber and the atmosphere. The process provides a means of controlling the time period during which the metering chamber is vented to the atmosphere, optimally allowing for a venting period of 300–500 milliseconds (ms), to prevent undesired air intrusion.

Actuating platform 26 is further connected to a reciprocating stroke 3-digit mechanical and digital counter 38 by a connecting rod 40 which advances counter 38 by one unit for each complete canister actuation/ recovery cycle. This arrangement provides a user with an indication of the number of doses of medication used or remaining in the canister. The counter may be reset to a base value when an exhausted MDI is replaced.

It will be understood that various details of the invention may be changed without departing from the scope of the invention. Furthermore, the foregoing description is for the purpose of illustration only, and not for the purpose of limitation as the invention is defined by the following, appended claims.

What is claimed is:

1. A device for use with a metered dose inhaler, the metered dose inhaler having a body with a nozzle block disposed therein, and an aerosol canister disposed in the body and movable relative to the nozzle block to dispense medicament from the metered dose inhaler, said device comprising:

a housing having a space therein configured for insertion, holding and removal of the metered dose inhaler from the space, said space communicating with an opening for dispensing of medicament from the metered dose inhaler therethrough;

means for automatically activating the metered dose inhaler by moving the canister relative to the body in response to inhalation of a user through said opening to vent the metered dose inhaler wherein a dose of medicament is dispensed therefrom; and return means for automatically deactivating the vented metered dose inhaler to an unvented position where medicament is no longer dispensed therefrom wherein said return means acts in response to said means for automatically activating the metered dose inhaler.

2. The device of claim 1 wherein said housing further comprises a hinged cap covering said opening when said cap is in a closed position and exposing said opening when said cap is in an open position.

3. The device of claim 2 wherein said cap is movable from its closed position to its open position to arm said means for depressing a metered dose inhaler.

4. The device of claim 1 further comprising control means for controlling time of venting of a metered dose inhaler.

5. The device of claim 1 further comprising a dosage counter for counting doses of medicament dispensed from a metered dose inhaler.

6. The device of claim 5 wherein said dosage counter is operatively connected to said means for depressing the metered dose inhaler.

7. The device of claim 1 wherein said means for activating a metered dose inhaler comprises:

an actuating platform for depressing a metered dose inhaler;

a power spring connected to said actuating platform for pulling said actuating platform to depress a metered dose inhaler; and a breath-activated catch and release member for catching and releasing said actuating platform.

8. The device of claim 1 wherein said housing comprises a movable access door for inserting and removing a metered dose inhaler.

9. A device for use with a metered dose inhaler to dispense medicament from the metered dose inhaler, said device comprising:

a housing having a space therein for holding a metered dose inhaler, said space communicating with an opening for dispensing of medicament from the metered dose inhaler therethrough, said housing including a hinged cap covering said opening when said cap is in a closed position and exposing said opening when said cap is in an open position;

an actuating platform within said housing for depressing the metered dose inhaler;

a power spring connected to said actuating platform, said power spring being stretchable so as to bias said actuating platform to depress the metered dose inhaler causing it to vent and dispense a dose of medicament therefrom;

a latch assembly within said housing, said latch assembly comprising a receiving member, a lower platform connected to said power spring opposite said actuating platform and an arm operatively connected to said cap such that movement of said cap from its closed position to its open position causes said arm to engage said receiving member and stretches said power spring away from said actuating platform;

a breath-activated member for maintaining said actuating platform in a fixed position and releasing said actuating platform in response to inhalation by a user; and a rod extending from said actuating platform toward said lower platform and positioned such that said rod contacts said lower platform during venting of the metered dose inhaler to release said receiving member from engagement with said arm and allow said actuating platform to move back to its fixed position.

10. The device of claim 9 further comprising a return spring connected to said actuating platform for pulling said actuating platform back to its fixed position.

11. A device for use with a metered dose inhaler to dispense medicament from the metered dose inhaler, said device comprising:

a housing having a space therein for holding a metered dose inhaler, said space communicating with an opening for dispensing of medicament from the metered dose inhaler therethrough;

means for automatically activating a metered dose inhaler in response to inhalation of a user through said opening to vent the metered dose inhaler where a dose of medicament is dispensed therefrom;

return means for automatically deactivating a vented metered dose inhaler to an unvented position where medicament is no longer dispensed therefrom wherein said return means acts in response to said means for automatically activating a metered dose inhaler; and control means for controlling time of venting a metered dose inhaler, said control means having a deformable viscoelastic element.

12. The device of claim 11 wherein said housing further comprises a hinged cap covering said opening when said cap is in a closed position and exposing said opening when said cap is in an open position.

13. The device of claim 12 wherein said cap is movable from its closed position to its open position to arm said means for depressing a metered dose inhaler.

14. The device of claim 11 further comprising a dosage counter for counting doses of medicament dispensed from a metered dose inhaler, said dosage counter being operatively connected to said means for depressing the metered dose inhaler.

15. The device of claim 11 wherein said means for activating a metered dose inhaler comprises:

an actuating platform for depressing a metered dose inhaler;

a power spring connected to said actuating platform for moving said actuating platform to depress a metered dose inhaler; and a breath-activated catch and release member for catching and releasing said actuating platform.

16. The device of claim 15 wherein said return means comprises:

a return spring connected to said actuating platform; and a rod extending from said actuating platform, said rod being adapted for releasing said power spring from a latched position during depression of said actuating platform whereby said rod and actuating platform can move to a position allowing a metered dose inhaler to be unvented.

17. The device of claim 11 wherein said housing comprises a movable access door for inserting and removing a metered dose inhaler.

18. A device for dispensing medicament, said device comprising:

a housing having a space therein for holding a conventional metered dose inhaler so as to allow insertion of the metered does inhaler into the space and removal of the metered dose inhaler from the space, said space communicating with an opening for dispensing of medicament from the metered dose inhaler therethrough;

means for automatically activating a metered dose inhaler in response to inhalation of a user through said opening to vent the metered dose inhaler where a dose of medicament is dispensed therefrom;

return means for automatically deactivating a vented metered dose inhaler to an unvented position where medicament is no longer dispensed therefrom wherein said return means acts in response to said means for automatically activating a metered dose inhaler; and a metered dose inhaler removably disposed within the housing, said metered dose inhaler comprising an container for holding medicament under pressure and an actuator for selectively engaging the container to allow release of medicament from the container.

* * * * *